United States Patent [19]
Takano et al.

[11] Patent Number: 5,446,175
[45] Date of Patent: Aug. 29, 1995

[54] OPTICALLY ACTIVE COMPOUNDS AND A METHOD FOR PRODUCING THEM

[75] Inventors: Seiichi Takano; Kunio Ogasawara, both of Sendai, Japan

[73] Assignee: Chisso Corporation, Osaka, Japan

[21] Appl. No.: 277,006

[22] Filed: Jul. 19, 1994

[30] Foreign Application Priority Data

Aug. 17, 1993 [JP] Japan .................................. 5-222748

[51] Int. Cl.$^6$ .................. C07D 301/00; C07D 303/32; C07D 49/527
[52] U.S. Cl. ...................................... 549/544; 549/513; 568/312; 568/315; 568/343; 568/347; 568/373
[58] Field of Search ................................. 549/544, 513

[56] References Cited

U.S. PATENT DOCUMENTS

| | | | |
|---|---|---|---|
| 3,979,338 | 9/1976 | Sundt ..................... | 549/544 |
| 4,031,237 | 6/1977 | Gough et al. ............ | 549/544 |
| 4,642,361 | 2/1987 | Ruttimann .............. | 549/544 |

OTHER PUBLICATIONS

Nomura et al, Hydration Of Several Monoterpene Hydrocarbons With Water In The Presence Of Synthetic Zeolites The Chemical Society of Japan, (1), 1992, p. 63–67.

Asaoka, et al, Enantioselective Routes To 2, 5–Disubstituted–And 4–Substitued–2–Cyclohexenones, Tetrahedron Letters, Vol. 30, No. 50, pp. 7075–7078, 1989.

*Primary Examiner*—Joseph E. Evans
*Attorney, Agent, or Firm*—Browdy and Neimark

[57] ABSTRACT

The present invention provides special epoxy derivative (1), cyclohexanone derivative (2), cyclohexenone derivative (3) and 3-substituted cyclohexenone derivative (4) which are useful as intermediates for synthesizing physiologically active materials, and a method for stereoselectively introducing substituted groups. Further, the present invention provides a method for synthesizing optically active compounds, such as optically active carvone via these intermediates.

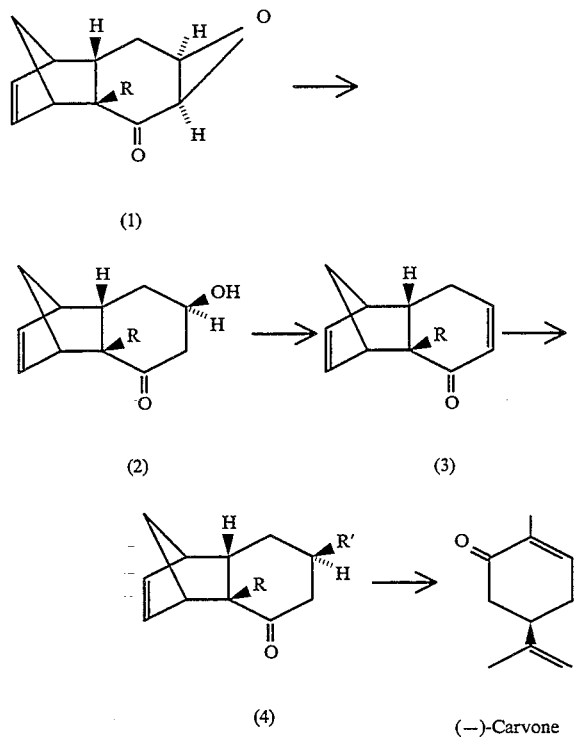

2 Claims, No Drawings

OPTICALLY ACTIVE COMPOUNDS AND A METHOD FOR PRODUCING THEM

BACKGROUND OF THE INVENTION

1. Field of the Invention

The present invention relates to epoxy derivatives useful as starting materials for synthesizing various physiologically active materials and a method of producing the derivatives, cyclohexanone derivatives, cyclohexenone derivatives, 3-substituted cyclohexanone derivatives, and a method of producing optically active carvone of perfume via these derivatives.

2. Description of the Prior Art

Epoxy derivatives, cyclohexanone derivatives, and 3-substituted cyclohexanone derivatives of the present inventions are widely useful as starting materials for synthesizing various physiologically active materials such as medicines and agricultural medicines, particularly these derivatives are very useful as starting materials for synthesizing optically active carbons of perfumes and their intermediates. Hitherto, a method for efficiently introducing substitution groups stereoselectively into cyclohexa-2, 5-diene skeletons (6) is unknown. For example, as a conventional method of optically active carvones, a reaction method of hydration of d-limonene with synthetic zeolite (Nihon Kagakukaishi, (1) , pages 63–67 (1992)), a method of stereoselective Grignard reaction with optically active 5-trimethylsilyl-2-cyclohexenone as a starting material (Takei et al, Tetrahedron Lett., 30, 7075 (1989)) and the like have been known. The former method is not stereoselective in the reaction, so that optically active carvone should be isolated from five kinds of products, the steps are troublesome and the product is obtained in low yield (30%). The latter method is stereoselective, but optically active 5-trimethylsilyl-2-cyclohexenone, which is a starting material having a stereoselectively 5-substituted group, should be obtained by repeated recrystallization of a diastereomer salt synthesized from a racemate of the starting material with cinchonidine and toluenethiol, and it is obtained in a low yield of 3% from racemic-5-trimethylsilyl-2-cyclohexenone. Thus, prior to the present invention, there is no industrially excellent method for producing efficiently optically active carvones.

Accordingly, it is desired to find an efficient method for producing optically active carvones. Further, it is desired to find optically active intermediates such as epoxy derivatives of the present invention obtained by deriving stereoselectively a substituted group, cyclohexanone derivatives, cyclohexenone derivatives, and 3-substituted cyclohexanone derivatives, which are widely applicable.

SUMMARY OF THE INVENTION

Considering the above, the inventors of the present invention have earnestly studied to obtain a retro synthetic method as shown in the following:

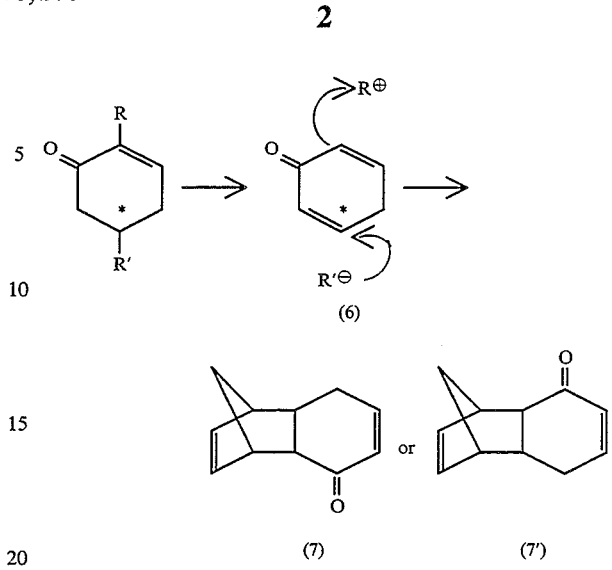

Namely, it has been found that several kinds of substituted groups are easily and stereoselectively introduced to 2,5-dienone (6) by using a compound (7) or (7') having a tricyclo ring skeleton as a starting material in good optical purities.

Further, by using the compound (7) having a tricyclo ring skeleton as a starting material, new useful epoxy derivative (1) or (1'), cyclohexanone derivative (2) or (2'), cyclohexenone (3) or (3') and 3-substituted cyclohexanone derivative (4) or (4') are obtained. Then, a method for efficiently obtaining the optically active compound represented by the formula (5) or (5') via the above derivatives.

In the present invention, the method is characterized in that, after the tricyclo ring compound (7) is epoxidized, a substituted group is stereoselectively introduced into the compound. The resultant compounds are epoxy derivatives represented by the formula:

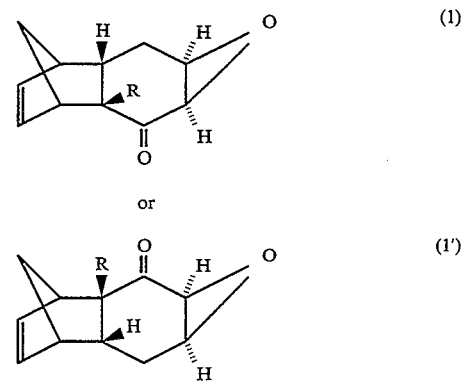

wherein R is alkyl, a hydrocarbon residue having at least one unsaturated bond, aralkyl or hydrogen, cyclohexanone derivatives represented by the formula:

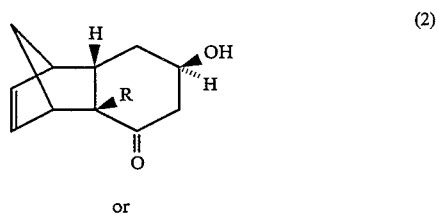

or

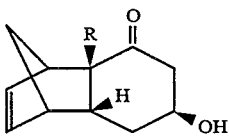
(2')

wherein R is alkyl, a hydrocarbon residue having at least one unsaturated bond, aralkyl or hydrogen, cyclohexenone derivatives represented by the formula:

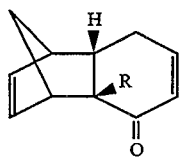
(3)

or

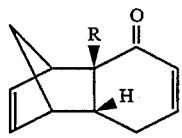
(3')

wherein R is alkyl, a hydrocarbon residue having at least one unsaturated bond, aralkyl or hydrogen, and 3-substituted cyclohexanone derivatives represented by the formula:

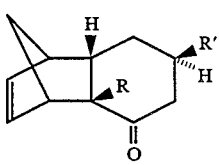
(4)

or wherein R is alkyl, a hydrocarbon residue having at least one unsaturated bond or aralkyl, R' is alkyl, a hydrocarbon residue having at least one unsaturated bond, aralkyl or a substituted group comprising hydrocarbon having trialkyl silyl in the skeleton, are provided. Moreover, a method for producing the epoxy derivatives represented by the formula (1) or (1') characterized in that the tricyclo ring skeleton compound (7) or (7') is epoxidized and a substituted group is stereoselectively introduced into the compound, and a method for producing the optically active compounds represented by the formula:

(5)

or (5')

via these derivatives is provided.

The optically active compound (7) or (7') having a tricyclo ring skeleton, which is a starting material, can be synthesized by the following method:

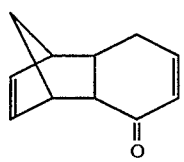
(7)

PdCl$_2$(PPh$_3$)$_2$
HCONH$_4$
dioxane or MeCN

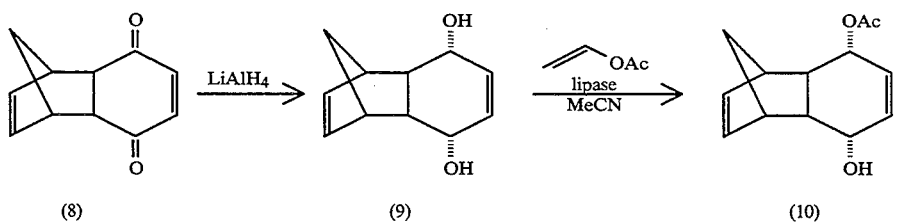

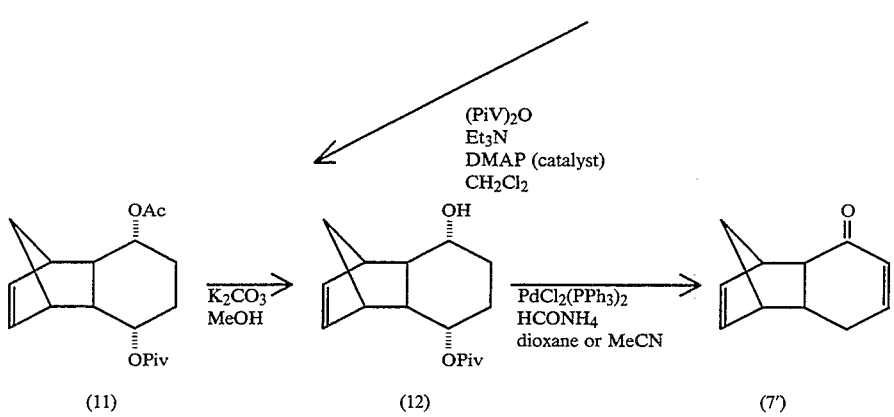

Namely, the compound (9) is obtained by reduction of a carbonyl group of the compound (8), which is obtained by Diels-Alder reaction with cyclopentadiene and hydroquinone, in the presence of a reducing agent such as lithium aluminum hydride. The resultant compound (9) is introduced to the compound (7) or (7') by a method of Takano et al (Japanese Patent Application Number 4-290684). In particular, the compound (9) is reacted by transesterification in a solvent such as acetonitrile with fatty acid vinyl esters in the presence of lipase PS (manufactured by Amano Pharmaceutical Co., Ltd.) derived from a Pseudomonas genus, and the optically active compound (10) can be obtained.

Compound (10) may be refluxed with ammonium bicarbonate in a solvent of dioxane or acetonitrile in the presence of bistriphenylphosphine palladium chloride to obtain the compound (7).

The compound (7'), which is an enantiomer of the compound (7), may be obtained by esterification of the compound (10) with pivaloylic acid anhydride, selective hydrolysis of the acetate of the resultant compound (11) with potassium carbonate, and reflux of the hydrolyzed compound in a solvent of dioxane or acetonitrile with ammonium bicarbonate in the presence of bistriphenylphosphine palladium chloride.

The method of producing optically active carvones using the resultant compound (7) as a starting material is shown in the following:

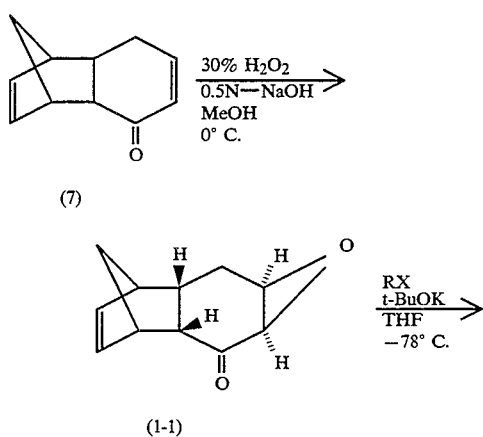

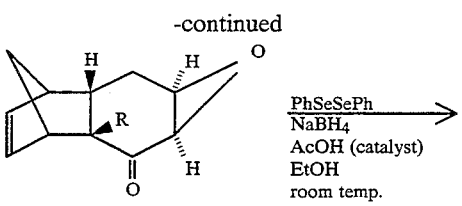

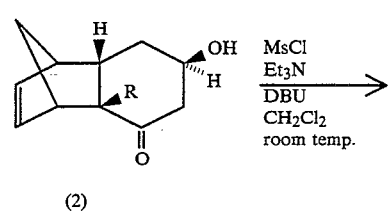

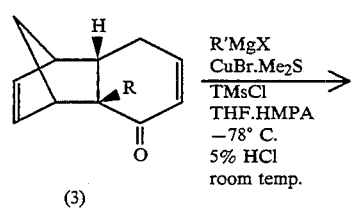

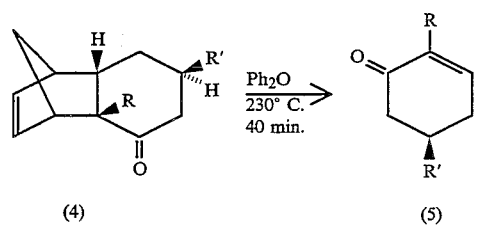

Firstly, the compound (7) is oxidized with an oxidizing agent such as hydroperoxide to obtain an epoxy derivative (1—1, R=H). Then, a halogenated material is derived from the epoxy derivative with a base for drawing protons such as potassium-t-butoxide and the epoxy derivative (1) having a substituted group is obtained. As halogens of the halogenated material, chlorine, bromine, iodine and the like are exemplified. As the substituted group, alkyl, a hydrocarbon residue having at least one unsaturated bond or aralkyl can be exemplified, and particularly methyl, ethyl, propyl, isopropyl, n-butyl, isobutyl, t-butyl, pentyl, hexyl, heptyl, octyl, vinyl, allyl, 1-butenyl, 2-butenyl, 1-pentenyl, 2-pentenyl, 3-pentenyl, 1,3-pentadienyl, cyclopropyl, cyclopentyl, 2-cyclopenten-1-yl, 3-cyclopenten-1-yl, 2-cyclohexen-1-yl, 3-cyclohexen-1-yl, phenyl, benzyl, o-tolyl, m-tolyl, p-tolyl, 2,3-xylyl, 2,4-xylyl, 3,5-xylyl, o-methoxyphenyl, m-methoxyphenyl, p-methoxyphenyl, o-benzyloxyphenyl, m-benzyloxyphenyl, p-benzyloxyphenyl, 2,3-dimethoxyphenyl, 2,4-dimethoxyphenyl, 3,5-dimethoxyphenyl, 2,3-dibenzyloxyphenyl, 2,4-dibenzyloxyphenyl and 3,5-dibenzyloxyphenyl.

Further, the epoxy derivative (1) may be reacted with a reducing agent such as sodium borohydride in the presence of diphenyl diselenide, and the oxysilane ring is stereoselectively reduced to obtain the cyclohexane derivative (2).

After the cyclohexane derivative (2) is mesylated with a halogenated sulfonyl compound such as mesyl chloride (MsCl), the resultant mesylate can be changed to the cyclohexenone derivative (3) by using a base such as 1,8-diazabicyclo[5.4.0]undeca-7-ene (DBU). The cyclohexenone derivative (3) may be changed to the 3-substituted cyclohexanone derivative (4) by a reaction for introducing substituted groups such as a Grignard reaction. Substituted group R' is alkyl, a hydrocarbon residue having at least one unsaturated bond, aralkyl or hydrocarbon residue having at least one trialkylsilyl in the skeleton, and particularly, methyl, ethyl, propyl, isopropyl, n-butyl, isobutyl, t-butyl, pentyl, hexyl, heptyl, octyl, vinyl, allyl, 1-propenyl, 1-butenyl, 2-butenyl, 3-butenyl, isopropenyl, 1,2-butadienyl, 1,3-butadienyl, 2,3-butadienyl, 1-pentenyl, 2-pentenyl, 3-pentenyl, 4-pentenyl, 1,2-pentadienyl, 1,3-pentadienyl, 1,4-pentadienyl, 2,3-pentadienyl, 2,4-pentadienyl, 3,4-pentadienyl, cyclopropyl, cyclopentyl, 2-cyclopentene-1-yl, 3-cyclopentene-1-yl, 2-cyclohexene-1-yl, 3-cyclohexene-1-yl, phenyl, benzyl, o-tolyl, m-tolyl, p-tolyl, 2,3-xylyl, 2,4-xylyl, 3,5-xylyl, o-methoxyphenyl, m-methoxyphenyl, p-methoxyphenyl, o-benzyloxyphenyl, m-benzyloxyphenyl, p-benzyloxyphenyl, 2,3-dimethoxyphenyl, 2,4-dimethoxyphenyl, 3,5-dimethoxyphenyl, 2,3-dibenzyloxyphenyl, 2,4-dibenzyloxyphenyl, 3,5-dibenzyloxyphenyl, trimethylsilylmethyl, 1-trimethylsilylethyl, 2-trimethylsilylethyl, 1-trimethylsilylpropyl, 2-trimethylsilylpropyl, 2-trimethylsilylpropyl, 3-trimethylsilylpropyl, 1-trimethylsilylvinyl, 2-trimethylsilylvinyl, trimethylsilylethynyl or the like.

In these compounds, 3-substituted cyclohexanone derivative (4) wherein R is Me and R' is isopropenyl can be changed to the (−)-carvone (5) by retro Diels Alder reaction.

Similarly, the antipode compound (7') having a tricyclo ring skeleton may be selected as a starting material to obtain the (+)-carvone (5').

The present invention can provide the following merits.

1. Derivatives represented by the above formulas (1) or (1'), (2) or (2'), (3) or (3'), and (4) or (4'), which are useful for synthesizing various physiologically active materials such as medicines and agricultural medicines, are obtained.

2. Various substituted groups can be stereoselectively introduced to the 2,5-dienone (6).

3. Through the derivatives represented by the formulas (1) or (1'), (2) or (2'), (3) or (3'), and (4) or (4') in order, optically active compounds represented by the formula (5) or (5') can be obtained.

DESCRIPTION OF THE PREFERRED EMBODIMENTS

The following examples illustrate the present invention more specifically, but these are not intended as a definition of the limits of the invention.

Reference Example 1

To an acetonitrile solution (5 ml) of a compound (9) (200 mg, 1.10 mol) and vinyl acetate (0.3 ml, 3.36 mmol), lipase PS (100 mg) was suspended, and the mixture was stirred for two weeks at room temperature. After the lipase was filtered away, the filtrate was concentrated under reduced pressure, and the residue was purified with a chromatograph over silica gel to obtain the colorless optically active compound (10) (193 mg, 79%).

Reference Example 2

To an acetonitrile solution 2 ml of the optically active compound (10) (100 mg, 0.45 mmol), ammonium bicarbonate (41 mg) and bistriphenylphosphine palladium chloride (3 mg, 0.004 mmol) were added, the mixture was refluxed for 20 minutes, and diethyl ether (10 ml) was added. The ether layer was washed with a saturated aqueous solution of sodium bicarbonate and with a saturated solution of sodium chloride, and then the organic layer was dried over magnesium sulfate. The solvent was distilled away under reduced pressure, and the residue was chromatographed over silica gel to obtain the compound (7) (72.2 mg, 90%).

Reference Example 3

To a dichloromethane solution (1 ml) of the optically active compound (10) (139 mg, 0.624 mmol), triethylamine (0.35 ml, 2.5 mmol), 4-dimethylamino pyridine DMAP (5 mg, 0.04 mmol) and pivalonic acid anhydride (0.38 ml, 1.9 mmol) were added, and the mixture was stirred for three days at room temperature. After water (5 ml) was added, the mixture was extracted with methylene chloride, the organic layer was washed with a saturated solution of sodium bicarbonate and with a saturated solution of sodium chloride, and the organic layer was dried over anhydrous magnesium sulfate. The solvent was distilled away under reduced pressure, the residue was chromatographed over silica gel to obtain the crude cyclohexene diester. The diester was dissolved in methanol (3 ml) as it is, potassium carbonate (50 mg, 0.36 mmol) was added, and the mixture was stirred for one hour. After methylene chloride was added, the organic layer was washed twice with a saturated solution of sodium chloride and dried over magnesium sulfate. The solvent was distilled away under reduced pressure, and the residue was chromatographed over silica gel to obtain the colorless solid compound (12) (132 mg, 80%).

Reference Example 4

Using the same method with Reference example 2 except that the compound (12) (94 mg, 0.359 mmol), ammonium carbonate (34 mg, 0.54 mmol), bistriphenylphosphine palladium chloride (2.5 mg, 0.0035 mmol) and acetonitrile (3 ml) were used, the compound (7') (57.6 mg, 90%) was obtained.

EXAMPLE 1

To a methanol solution (20 ml) of the compound (7) (1.83 g, 11.4 mol), a 0.5M solution (2.5 ml) of sodium hydroxide and a 30% (w/v) hydroperoxide solution (2.0 ml, 17.4 mmol) were added on ice cooling and the mixture was stirred for 20 minutes. Methylene chloride (20 ml) was added to the reaction mixture, and the mixture was washed with water and with a saturated solution of sodium chloride. The organic layer was dried over anhydrous magnesium sulfate, and the solvent was distilled away under reduced pressure. The residue was chromatographed over silica gel to obtain a colorless solid of the epoxy derivative (1—1) (1.82 g, yield 90%).

m.p.: 51°-52.5° C.; $[\alpha]_D^{30}$ —9.6° (c 1.10, CHCl$_3$);

IR (neat): 1710 cm$^{-1}$;

$^1$H-NMR (300 MHz, CDCl$_3$) δ: 1.14 (d, 1H, J=8.4 Hz), 1.22 (dd, 1H, J=14.7, 10.6 Hz), 1.31 (d, 1H, J=8.4 Hz), 2.28 (ddd, 1H, J=14.7, 6.6, 3.7 Hz), 2.61–2.74 (m, 2H), 2.78 (dd, 1H, J=10.2, 3.3 Hz), 2.98 (br. s, 1H), 3.03 (d, 1H, J=4.4 Hz), 3.31 (t, 1H, J=4.4 Hz), 5.76–5.79 (m, 1H), 6.08–6.10 (m, 1H);

$^{13}$C-NMR (75 MHz, CDCl$_3$) δ: 27.40, 36.25, 42.85, 45.43, 47.58, 50.50, 54.47, 57.47, 133.97, 138.39, 209.28

MS m/z: 176 (M$^+$), 66 (100%);

HRMS Calcd. C$_{11}$H$_{12}$O$_2$: 176.0837. Found: 176.0850;

Anal Calcd. C$_{11}$H$_{12}$O$_2$: C,74.97, H,6.86 Found: C,74.85, H,6.99

EXAMPLE 2

To a solution of potassium t-butoxide (694 mg, 6.18 mmol) in THF (6 ml), a solution of epoxy derivative (1—1) (545 mg, 3.10 mmol) in THF (5 ml) was added dropwise with stirring at −78° C. After the mixture was stirred for one hour, methyl iodide (0.60 ml, 9.6 mmol) was added and stir for more one hour at the same temperature. To the resulting reaction mixture, a saturated aqueous solution (10 ml) of ammonium chloride was added, and the temperature was raised to room temperature. After the reaction mixture was extracted with diethyl ether, extracted liquid was washed with a saturated aqueous solution of sodium bicarbonate and with a saturated aqueous solution of sodium chloride. Then, the organic layer was dried over anhydrous magnesium sulfate, and the solvent was distilled away under reduced pressure. The residue was chromatographed over silica gel to obtain the colorless solid epoxy derivative (1) (R=Me, 497 mg, yield 84%).

m.p.: 60°-61° C.; $[\alpha]_D^{29}$ +94.3° (c 1.37, CHCl$_3$);

IR (nujol): 1708 cm$^{-1}$;

$^1$H-NMR (300 MHz, CDCl$_3$) δ: 1.32–1.42 (m, 2H), 1.42 (s, 3H), 1.55 (d, 1H, J=8.8 Hz), 2.29 (td, 1H, J=10.5, 3.3 Hz), 2.48 (ddd, 1H, J=14.7, 7.7, 3.3 Hz), 2.77 (br. s, 2H), 3.17 (d, 1H, J=4.0 Hz), 3.43 (t, 1H, J=4.2 Hz), 5.93 (dd, 1H, J=5.5, 2.9 Hz), 6.25 (dd, 1H, J=5.5, 2.9 Hz);

MS m/z: 190 (M$^+$), 66 (100%);

HRMS Calcd. C$_{12}$H$_{14}$O$_2$: 190.0994 Found: 190.1004;

Anal Calcd. C$_{12}$H$_{14}$O$_2$, C,75.76, H,7.42 Found: C,75.55, H,7.47

EXAMPLE 3

To an ethanol solution (25 ml) of diphenyldiselenide (1.45 g, 4.64 mmol), sodium boron hydride (343 mg, 9.2 mmol) was slowly added on ice cooling. After the mixture was stirred for 50 minutes at room temperature, acetic acid (0.09 ml, 1.5 mmol) was added. After stirring for 30 minutes, an ethanol solution (5 ml) of the epoxy derivative (1) (441 mg, 2.32 mmol) was added dropwise to the mixture. After the mixture was stirred for 12 hours, water was added, and the mixture was extracted with ethyl acetate. The extract was washed with a saturated aqueous solution of sodium bicarbonate, and with a saturated aqueous solution of sodium chloride. The organic layer was dried over anhydrous magnesium sulfate, and the solvent was distilled away under reduced pressure. The residue was chromatographed over silica gel to obtain the colorless oily cyclohexanone derivative (2) (R=Me, 400 mg, yield 90%).

$[\alpha]_D^{29}$ —89.6 (c 1.30, CHCl$_3$);

IR (neat): 1690 cm$^{-1}$;

$^1$H-NMR (300 MHz, CDCl$_3$) δ: 1.14–1.24 (m, 1H), 1.44(s, 3H), 1.61 (br. s, 3H), 2.10–2.19(m, 2H), 2.41–2.46 (m, 2H), 2.83 (br. s, 1H), 2.88 (br. s, 1H), 4.25 (br. s, 1H), 6.03–6.06 (m, 1H), 6.17–6.20 (m, 1H);

$^{13}$C-NMR (75 MHz, CDCl$_3$) δ:27.34, 35.14, 44.36, 46.12, 47.02, 47.48, 52.01, 54.83, 66.27, 135.22, 139.06, 217.18;

MS m/z: 192 (M$^+$), 66 (100%);

HRMS Calcd. C$_{12}$H$_{16}$O$_2$: 192.1151 Found: 192.1142

EXAMPLE 4

To a methylene chloride solution (5 ml) of the cyclohexanone derivative (2) (R=Me, 400 mg, 2.08 mol), 1,8-diazabicyclo [5.4.0]undeca-7-ene (0.31 ml, 2.0 mmol), triethyl amine (0.58 ml, 4.2 mmol) and mesyl chloride (0.24 ml, 3.1 mmol) were added on ice cooling, and the mixture was stirred at room temperature for 3 hours. Further, 1,8-diazahicyclo [5.4.0] 7-ene (0.31 ml, 2.0 mmol) and mesyl chloride (0.08 ml, 1.0 mmol) were added to the mixture and the mixture was stirred at room temperature for 2 hours. Water was added to the resulting reaction mixture. After the mixture was extracted with diethyl ether, the organic layer was washed with a saturated aqueous solution of sodium bicarbonate and with a saturated solution of sodium chloride- Then, the organic layer was dried over anhydrous magnesium sulfate, and the solvent was distilled away under reduced pressure. The residue was chromatographed over silica gel to obtain the colorless solid cyclohexenone derivative (3) (R=Me, 338 mg, yield 93%).

m.p.: 87°-88° C.; $[\alpha]_D^{29}$ —144° (c 0.994, CHCl$_3$);

IR (neat): 1660 cm$^{-1}$, $^1$H-NMR (300 MHz, CDCl$_3$) δ:1.29 (s, 3H), 1.29–1.31 (m, 1H), 1.49 (d, 1H, J=8.8 Hz), 1.95 (dd, 1H, J=20.9, 3.3 Hz), 2.23 (dt, 1H, J=10.2, 3.3 Hz), 2.59 (ddt, 1H, J=20.9, 10.2, 3.1 Hz), 2.81 (hr. s, 1H), 2.86 (br. s, 1H), 5.72 (br. d, 1H, J=10.2 Hz), 5.97–6.07 (m, 2H), 6.55 (dt, 1H, J=9.9, 4.0 Hz);

$^{13}$C-NMR (75 MHz, CDCl$_3$) δ: 27.63, 27.81, 47,87, 45.55, 49.50, 52.02, 53.14, 128.43, 134.06, 139.54, 147.90, 203.76;

MS m/z: 176 (M$^+$), 66 (100%);

HRMS Calcd. C$_{12}$H$_{14}$O: 74.1045 Found: 174.1063;

Anal Calcd. C$_{12}$H$_{14}$O: C,82.72, H,8.10 Found: C,82.97, H,7.97

EXAMPLE 5

To a mixture of copper bromide-dimethyl sulfide complex (8 mg, 39 μmol) and a THF solution (4ml) of hexamethylphosphoamide (0.26 ml, 1.54 mmol), a THF solution (0.74 ml, 0.71 mmol) of 0.96M isopropenyl magnesium bromide was added dropwise with stirring at −78° C. After ten minutes, cyclohexenone derivative (3) (R=Me, 130 mg, 0.74 mol) and a THF solution (2 ml) of trimethylsilyl chloride (0.19 ml, 1.5 mmol ) was added dropwise to the mixture, and the mixture was stirred for one hour at the same temperature. 5% hydrochloric acid (1 ml) was added to the resulting reaction mixture, and the mixture was stirred for 30 minutes at room temperature and extracted with diethyl ether. The extract was washed with water, with a saturated aqueous solution of sodium bicarbonate and with a saturated aqueous solution of sodium chloride. The organic layer was dried over anhydrous magnesium sulfate, and the solvent was distilled away under reduced pressure. The residue was chromatographed over silica gel to obtain the colorless oily 3-substituted cyclohexane derivative (4) (R=Me, R'-isopropenyl, 138 mg, yield 86%). $[\alpha]_D^{29}+22.2°$ (c 1.32, CHCl$_3$);

IR (neat): 1707, 1652 cm$^{-1}$;

$^1$H-NMR (300 MHz, CDCl$_3$) δ: 1.31 (s, 3H), 1.36 (dt, 1H, J=8.4, 1.8 Hz), 1.53 (d, 1H, J=8.8 Hz), 1.67 (s, 3H), 1.70–1.91 (m, 2H), 2.09–2.17 (m, 2H), 2.21–2.29 (m, 2H), 2.75 (br. s, 1H), 2.87 (br. s, 1H), 4.62 (s, 1H), 4.72 (s, 1H), 6.10–6.15 (m, 2H);

$^{13}$C-NMR (75 MHz, CDCl$_3$) δ: 20.78, 27.46, 31.86, 38.43, 44.55, 46.62, 47.41, 49.98, 52.60, 54.94, 109.75, 134.76, 139.37, 147.64, 216.89;

MS m/z: 21 6 (M+), 66 (100%);

HRMS Calcd. C$_{15}$H$_{20}$O: 216.1515 Found: 216.1485;

Anal Calcd. C$_{15}$H$_{20}$O: C,83.28, H,9.32 Found: C,83.08, H,9.37

EXAMPLE 6

A diphenyl ether solution (4 ml) of 3-substituted cyclohexanone derivative (4) (R=Me, R '=isopropenyl, 118 mg, 0.54 mmol) was heated at 240° C. for 30 minutes. After cooling to room temperature, the reaction mixture was chromatographed over silica gel (10 g) to obtain colorless oily (−)-carvone (72 mg, yield 88%), $[\alpha]_D^{30}$ −52.3° (c 1.17, CHCl$_3$).

We claim:

1. An epoxy derivative represented by the general formula:

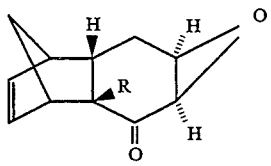

(1)

or

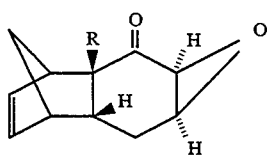

(1')

wherein R is alkyl, a hydrocarbon residue having at least one unsaturated bond, aralkyl or hydrogen.

2. A method for producing an epoxy derivative of claim 1, the method comprising:

epoxidizing optically active tricyclo undeca-4,9-diene-1 -on; and stereo selectively obtaining the epoxy derivative represented by the formula (1) or (1').

* * * * *